United States Patent [19]

Nakajima

[11] Patent Number: 4,974,075
[45] Date of Patent: Nov. 27, 1990

[54] IMAGE PICKUP APPARATUS HAVING CONNECTOR CAPABLE OF SEPARATELY SHIELDING GROUPED ELECTRICAL CONNECTIONS

[75] Inventor: Shigeru Nakajima, Fuchu, Japan

[73] Assignee: Olympus Optical Co., Ltd., Tokyo, Japan

[21] Appl. No.: 221,976

[22] Filed: Jul. 20, 1988

[30] Foreign Application Priority Data

Aug. 11, 1987 [JP] Japan .................... 62-200293

[51] Int. Cl.⁵ .................... H04N 7/18; H01R 13/648; F21V 7/04; A61B 1/00
[52] U.S. Cl. .................... 358/98; 128/4; 439/579; 439/607; 439/610
[58] Field of Search .................... 358/98; 439/379, 607, 439/608, 609, 610, 675, 909, 582, 592, 668; 128/4, 6, 46

[56] References Cited

U.S. PATENT DOCUMENTS

| | | | |
|---|---|---|---|
| 2,804,601 | 8/1957 | Harthman et al. | 439/607 X |
| 4,340,265 | 7/1982 | Ott et al. | 439/579 |
| 4,414,608 | 11/1983 | Furihata | 128/4 X |
| 4,457,574 | 7/1984 | Walters | 439/610 |
| 4,537,453 | 8/1985 | Takeuchi | 439/217 |
| 4,558,918 | 12/1985 | Shores | 439/579 |
| 4,565,423 | 1/1986 | Ueda | 358/98 X |
| 4,574,783 | 3/1986 | Kazuhiro et al. | 128/4 |
| 4,607,621 | 10/1986 | Wheeler | 128/6 |
| 4,615,330 | 10/1986 | Nagasaki et al. | 128/4 |
| 4,674,822 | 6/1987 | Hall | 439/607 X |

*Primary Examiner*—Howard W. Britton
*Assistant Examiner*—Mark R. Powell
*Attorney, Agent, or Firm*—Armstrong, Nikaido, Marmelstein, Kubovcik & Murray

[57] ABSTRACT

An electrical connector for electrically connecting an image pickup unit and a system for processing signals supplied therefrom. Signal cables are separated into some groups so that signals in different cables in each group do not considerably interfere with each other. The groups of cables are respectively shielded by shielding members, and an inner conductor of each shielded signal cable is connected to a contact of a single-pin structure for electrical connection to a corresponding conductor while shielding members are electrically connected by electrical contacts of a single-pin structure.

3 Claims, 11 Drawing Sheets

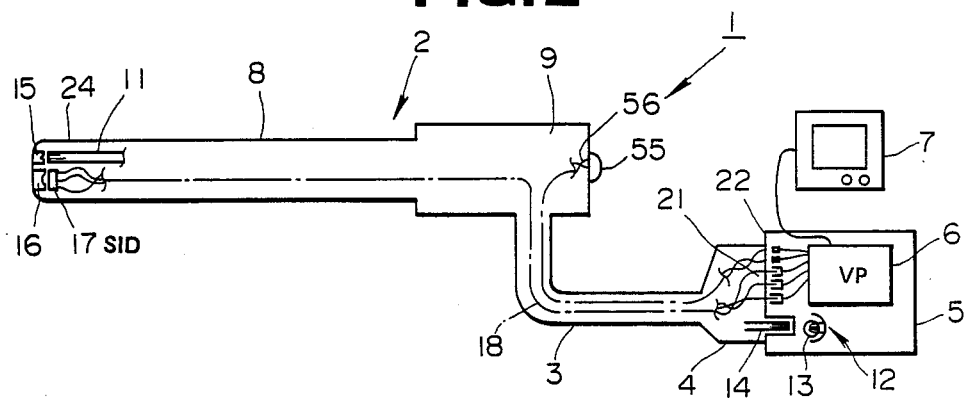
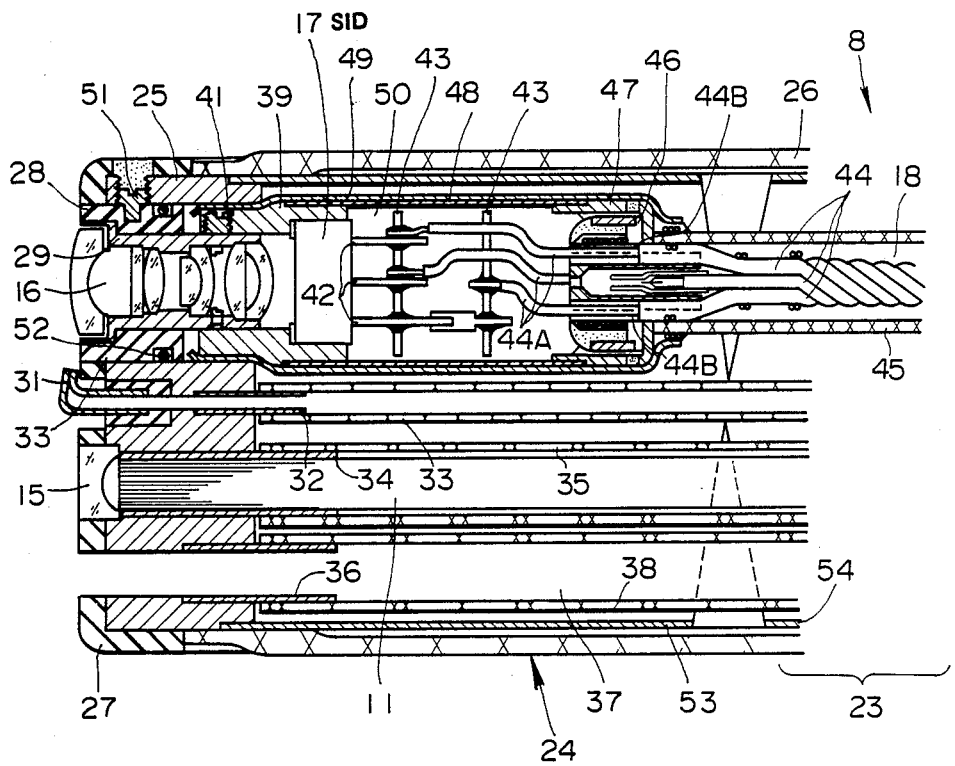

IMAGE PICKUP APPARATUS HAVING CONNECTOR CAPABLE OF SEPARATELY SHIELDING GROUPED ELECTRICAL CONNECTIONS

BACKGROUND OF THE INVENTION

This invention relates to an image pickup apparatus having an electrical connector in which electrical connections constituted by groups of a plurality of single-pin contacts can be shielded with respect to each group.

An image pickup apparatus which makes use of, as an image pickup means, a solid-state image pickup device (hereinafter referred to simply as "SID") such as a charge coupled device (hereinafter referred to as "CCD") has lately been put to practical use.

This image pickup device incorporates the SID in an image pickup section and is capable of forming an image on a monitor display as well as recording the image in a VTR or the like by temporarily converting the corresponding optical image into an electrical signal and processing the converted signal in a video processor (hereinafter referred to as "VP").

The SID signal cable simultaneously transmits signals at various frequencies including a current (dc) from a drive source, an output signal (several MHz), horizontal synchronization pulses (several MHz), and vertical synchronization pulses (several tens KHz). In general, signals are supplied via a shielded line using coaxial cables since, as is well-known, a high-frequency signal disturbs a low frequency signal (that is, generates a noise therein). Pairs of coaxial contacts are also employed to establish connection between a video camera and a VP.

However, the use of coaxial contacts increases the outside dimensions of the connector as well as the force required to disconnect the connector, makes the durability of the connector during repeated connecting and disconnecting operations incommensurably inferior, and makes it difficult to construct the connector with a waterproof structure. For example, in an electronic endoscope which is a type of video camera, a connector is constituted by coaxial contacts although it needs to have small outside dimensions, to be capable of being disconnected by a small force and to be improved in durability. The construction of this connector conflicts with these requirements. The size and weight of this type of connector may be further increased as the picture element density of the SID and, hence, the number of contacts will be increased. Recently, a new structure of subminiature coaxial contacts has been developed, but it is not practical since it lowers the durability.

SUMMARY OF THE INVENTION

It is therefore an object of the present invention to provide an image pickup apparatus having an electrical connector which has improved durability against repeated connecting and disconnecting operations while being reduced in size.

It is another object of the present invention to provide an image pickup apparatus having an electrical connector which enables a high signal to noise ratio (S/N).

To these ends, the present invention provides an electrical connector in which signal cables respectively shielded are separated into some groups so that signals on different cables in each group do not considerably interfere with each other and in which inner conductors of signal cables in each group are connected to electrical contacts of a single-pin structure while outer conductors of these cables are connected in common or connected to a plurality of contacts of a single-pin structure and are also connected to a shielding member provided between the groups cables. The connector is being improved in durability and S/N (signal to noise ratio) as well as being reduced in size.

BRIEF DESCRIPTION OF THE DRAWINGS

FIGS. 1 to 3 relate to a first embodiment of the present invention;

FIG. 1 is a perspective view of a signal connector and a signal connector receiver in accordance with the first embodiment;

FIG. 2 is a diagram of the entire constitution of the first embodiment;

FIG. 3 is a cross-sectional view of the structure of a head of an electronic endoscope;

DESCRIPTION OF THE PREFERRED EMBODIMENTS

Figure 1:
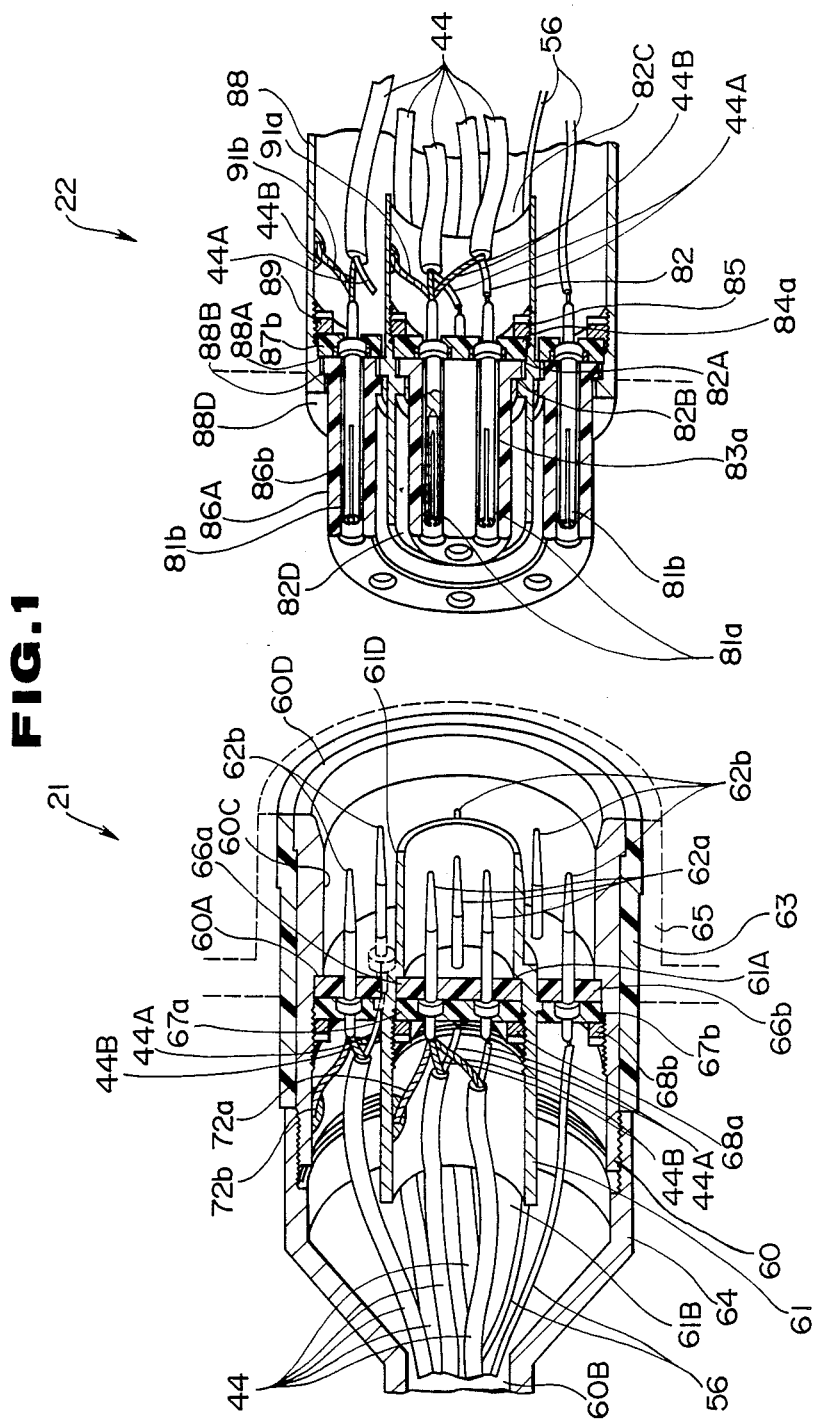

Referring to FIG. 2, an image pickup apparatus which embodies the present invention is constituted by an electronic endoscope (electronic scope) 2, a signal processing unit 5 to which a connector 4 attached to an end of a universal cord 3 of the electronic scope 2 can be connected, a monitor 7 which is connected to a video processor 6 (hereinafter referred to simply as "VP") provided in the signal processing unit 5 and which displays images.

The electronic scope 2 has an elongated insertion portion 8 designed to be easily inserted into a body cavity or the like. An operational portion 9 is provided at the rear end of the insertion portion 8.

A light guide 11 for transmitting illumination light is inserted into and extended through the insertion portion 8. The light guide 11 is also inserted into and extended through the universal cord 3 extending from the operational portion 9 to the outside. The connector 4 is connected to the signal processing unit 5. Illumination light emitted from a light source lamp 13 constituting a light source 12 housed in the signal processing unit 5 is thereby introduced to an incidence end surface of the light guide 11 at which a illumination connector 14 is formed.

Illumination light supplied from the light source lamp 13 to the incidence end surface is transmitted through the light guide 11 to an emission end surface thereof and is emitted to a subject through an illumination lens 15 disposed in front of the emission end.

An image of the subject illuminated by the light emitted through the illumination lens 15 is formed by an objective 16 attached to the end of the insertion portion 8 on a solid-state image pickup device (SID) 17 disposed on a focal plane of the objective 16.

An end of a signal cable 18 having a plurality of signal lines is connected to the SID 17. The signal cable 18 is extended through the insertion portion 8 and the universal cord 3, and is connected at its other end to a signal connector (or electrical connector) 21 provided in the connector 4. The signal connector 21 is connected to a signal connector receiver (or electrical connector receiver) 22 provided in the signal processing unit 5, thereby being connected to the VP 6.

The insertion portion 8 has a curving portion 23 (FIG. 3) formed at its flexible portion, and a head 24 formed in front of the curving portion 23.

As shown in FIG. 3, a head member 25 which forms the head 24 is generally cylindrical and is formed of a ceramic or the like. An end of an outer casing 26 having insulating properties is fixed to an outer peripheral surface of the head member 25, and outer and front-end surfaces of a front portion of the head member 25 are covered with a head cover 27 having an insulating property.

The head member 25 has a through hole which extends in parallel with the axis of the cylindrical form of the head member 25 and to which the objective 16 mounted in a lens frame 29 is attached, an insulating frame 28 being interposed between the lens frame 29 and the head member 25.

A nozzle 31 is disposed in a hole having a smaller diameter formed adjacently to the objective 16 so that it projects toward the outer surface of the objective 16. The nozzle 31 communicates with an air/water supply path of an air/water supply tube 33 attached to the head member 25 at the rear end of the small hole by an adapter member 32.

Another through hole is formed in the head member 25, and the emission end of the light guide 11 is fixed to this hole by an adapter member 34. The adapter member 34 fixed to this through hole projects rearward, and the front end of a tube 35 which covers the light guide 11 is fixed to the adapter member 34. The illumination lens 15 is mounted in front of the emission end of the light guide 11. There is still another through hole in the head member 25 to which the front end of a tube 38 which forms a clamp channel 37 is fixed by an adapter member 36.

An SID frame 39 in which the SID 17 is mounted is fitted around the lens frame 29 and is fixed by a vis 41. The SID frame 39 is slid relative to the lens frame 29 and is thereby adjusted to a position at which the light receiving plane of the SID 17 coincides with the focal plane, thereafter being fixed by the vis 41.

Leads 42 are protrusively formed on the reverse surface (rear surface) of the SID 17, are extended across, for example, a pair of supports 43 disposed in parallel with each other, and are connected to inner conductors 44A of shielding wires 44 in the signal cable 18.

The signal cable 18, that is provided as, for example, a twisted cable, is inserted into and led through a protective tube 45, outer conductors 44B of the signal cable 18 is fixed to a cable stop 46 by soldering or the like at the rear of the supports 43. The cable stop 46 is fixed to a pipe stop 47 to which the rear end of a pipe 48 whose front end is fixed to the outer periphery of the SID frame 39 is fixed. The outer peripheral surface of the pipe 48 is covered with an insulating tube 49 which is extended forward over the front end of the outer peripheral surface of the SID frame 39 while being extended rearward over the rear end of the cable stop 46 so that the insulating tube 49 covers an electrical equipment portion 50 which includes electrical attachment portions between the SID 17 and the end of the signal cable connected to the leads 42 of the SID 17. The electrical equipment unit 50 is shielded by the lens frame 29 made of a metal, the SID frame 39 made of a metal fitted to the lens frame 29 and fixed by the vis 41, the pipe 48 made of a metal having its front end fixed to the SID frame 39, the pipe stop 47 made of a metal to which the rear end of the pipe 48 is fixed, and the cable stop 46 made of a metal fixed to the pipe stop 47.

The electrical equipment portion 50 insulated by and covered with the insulating tube 49 is assembled in such a manner that the lens frame 29 fixed to the SID frame 39 is fitted into the through hole of the head constituent member (from the rear thereof) and is fixed by a vis 51. After being fastened by the vis 51, the electrical equipment portion is fixed by an adhesive. The electrical equipment portion 50 can be replaced or repaired after being detached from the head member 25 by removing the vis 51.

A circumferential groove is formed in the outer peripheral surface of the insulating frame 28, and an O-ring 52 for constituting a watertight portion is accommodated in this groove.

Since the outer peripheral portion of the SID frame 39 is covered with the insulating tube 49, the shielded portion of the electrical equipment portion 50 is not electrically communicated with the head member 25 when the electrical equipment portion 50 is attached thereto. The electrical equipment portion 50 is thus shielded, thereby preventing intrusion of any external noise in a case where the electronic scope is used while a high-frequency treatment instrument is inserted into the clamp channel 37.

The electrical equipment portion 50 is accommodated in a cylindrical pipe 53 having its front end fixed to the head member 25. A curving piece 54 is pivotally supported at the rear of the cylindrical pipe 53, and the curving portion 23 is formed at the rear of this pivot support point to a desired length. As shown in FIG. 2, a switch 55 is provided in the operational portion 9. The switch 55 is connected to the VP 6 via single wires 56 and is used to change over a moving image and a still image.

FIG. 1 shows the structure of the signal connector 21 and the signal connector receiver 22 that are essential portions of the first embodiment.

Basically, the connector 21 is constructed in such a manner that the plurality of signal lines 44 are grouped with respect to high-frequency use and low-frequency use, and high-frequency and low-frequency signal lines thereby grouped are respectively connected to metallic contact pins 62a and 62b of a single-pin structure disposed in inner and outer regions partitioned by an inner shielding frame 61 provided in an outer shielding frame 60. The connector receiver 22 to which the connector 21 is connected has a similar structure.

The connector 21 has a metallic shielding frame 64 which has a threaded hole at the side of a base portion of the outer metallic shielding frame 60 covered with an insulating frame 63 and which is detachable from the connector 21. The insulating frame 63 is covered with a (metallic) outer connector member 65 indicated in the broken line in FIG. 1.

The shielding frame 60 is in the form of a cylinder, and a disklike insulator plate 66b having a circular opening formed at its center and an insulator plate 67b having a similar configuration and superposed on the insulator plate 66b are fixed inside the shielding frame 60 by screwing a fastening ring 68b having a threaded outer peripheral surface into the threaded hole that forms an inner peripheral surface of the shielding frame 60. The inner shielding frame 61 is fitted into the opening formed at the center of the insulator plate 66b. A disklike insulator plate 66a and an insulator plate 67a having a similar configuration superposed on the insulator plate 66a are disposed inside the shielding frame 61 and are fixed by a fastening ring 68a.

A plurality of small holes are formed in the insulator plates 66a and 66b and insulator plate 67a and 67b superposed on the former. The contact pins 62a and 62b of the single-pin structure pass through these holes.

Each of the contact pins 62a and 62b has a flange or a portion having an increased diameter and formed on its intermediate portion near its base portion. The flanges of the contact pins 62a and 62b are fitted into increased-diameter stepped portions of the holes formed in the insulator pates 67a and 67b, thereby limiting the movements of these flanges. In this state, the flanges are fixed by the fastening rings 68a and 68b.

The shielding frames 60 and 61 have stepped portions 60A and 61A. These frames have reduced inside diameters on the front side of these stepped portions. The insulator plates 66b and 66a are inhibited from moving forward by being respectively brought into abutment against the stepped portions 60A and 61A, and they are fixed by the fastening rings 68a and 68b.

Each of some of the signal lines 44 in the signal cable 18 grouped for high-frequency use is separated into an inner conductor 44A and an outer conductor 44B at its end portion located inside the inner shielding frame 61 at a distance from an opening 61B formed at the base end of this frame equal to or greater than the radius thereof. The outer conductors 44B are gathered and connected by soldering to one of the contact pins 62a inside the inner shielding frame 61 and are also connected by soldering to an inner wall surface of the shielding frame 61 via a shielding connection wire 72a. The inner conductors 44A are respectively connected to the other contact pins 62a by soldering.

Each of some of the signal lines 44 grouped for low-frequency use is separated into an inner conductor 44A and an outer conductor 44B at its portion located inside the outer shielding frame 60 at a distance from an opening 60B formed at the based end of this frame equal to or greater than the radius thereof. The outer conductors 44B are gathered and connected by soldering to an inner wall surface of the shielding frame 60 via a shielding connection wire 72b and are also connected by soldering to one of the contact pins 62b. The inner conductors 44A are respectively connected by soldering to base ends of the other contact pins 62b.

The base end of the outer shielding frame 60 is threaded so that the shielding frame 64 is detachably attached to the shielding frame 60 by being screwed around the threaded portion. The shielding frame 60 is fixed to the metallic outer connector member 65 that becomes a high-frequency noise source at the time of treatment using a high-frequency treatment instrument.

The single wires constituting the signal line 56 are connected to connection pins 62b disposed outside the shielding frame 61.

In the connector receiver 22, metallic contact pin receivers 81a and 81b which serve as members for receiving the contact pins 62a and 62b are separately disposed on the inside and outside of a metallic shielding frame 82. The contact pin receivers 81a are put between an insulator member 83a and an insulator plate 84a which are brought into abutment against stepped portions 82B and 82A of the shielding frame 82 and which are fastened and fixed by a fastening ring 85. The insulator plate 84a is securely fixed by the stepped portion 82A and the fastening ring 85, but the insulator member 83a is not tightly fastened while it is only put between the insulator plate 84a and the stepped portion 82B and there is a clearance around the insulator member 83a in the diametral direction, thereby enabling the insulator member 83a to be shifted in the diametral direction to a position suitable for receiving the contact pins 62a of the connector 21 even if these pins are not correctly centered when introduced into the connector receiver.

The contact pin receivers 81b disposed outside the shielding frame 82 is put between an insulator member 86b and an insulator plate 87b which are brought into abutment against stepped portions 88B and 88A of an metallic outer shielding frame 88 and which are fastened and fixed by a fastening ring 89. In this case also, the shielding frame 82, the insulator member 86b and the contact pin receivers 81b can be slightly shifted in the diametral direction. The contact pin receivers 81a inside the shielding frame 82 can also be shifted slightly in the diametral direction.

The contact pin receivers 81a and 81b are connected to the signal lines 44. Branching portions at which the inner conductors 44A and the outer conductors 44B of the group of signal lines 44 for high-frequency use diverge are located inside the inner shielding frame 82 at a distance from an opening 82C equal to or greater than the radius thereof (at the left-hand side of the opening as viewed in FIG. 1). Similarly, branching portions of the low-frequency groups are located inside the outer shielding frame 88 at a distance from an opening (not shown) of this frame equal to or greater than the radius thereof.

The contact pin receivers 81a and 81b to which the outer conductors 44B are connected are electrically connected by soldering or the like to inner wall surfaces of the inner shielding frame 82 and the outer shielding frame 88 via shielding connection wires 91a and 91b, respectively.

The inner conductors 44A of the group of signal lines 44 for high-frequency use are connected to the contact pin receivers 81a while the group of inner conductors 44A for low-frequency use are connected to the contact pin receivers 81b.

When the connector 21 is connected to the connector receiver 22, the contact pins 62a and 62b are respectively inserted into the contact pin receivers 81a and 81b, thereby establishing electrical connections. The inner shielding frame 61 is inserted into the connector receiver 22 with an adequate clearance between its front-end outer peripheral portion 6D and a front-end inner peripheral portion 82D of the shielding frame 82 (to reduce the force required to insert the connector). Therefore, these frames are not specially intended to directly establish electrical connection but some portions may be electrically connected by being accidentally brought into contact with each other owing to, for example, dispersion of dimensions or eccentricity. The electrical connection between the shielding frame 61 and the shielding frame 82 is positively established by the connection between the contact pin 62a and the contact pin receiver 81a connected to the high-frequency outer conductors 44B. The outer shielding frame 60 is fitted into the connector receiver 22 with an adequate clearance between its front-end inner surface 60C and an outer peripheral surface 86A of the outer insulator member 86b, and the front-end inner surface 60C serves as a guide for insertion or detachment of the connector 21 into or from the connector receiver 22. A front-end surface 60D of the outer shielding frame 60 abuts against a front-end surface 88D of the outer shielding frame 88. Formation of a certain gap between the front-end surfaces 60D and 88D may be allowed so long as the gap is small enough to prevent intrusion of any considerable noise. Electrical connection between the front-end surfaces 60D and 88D may be established but it is not always necessary. The outer shielding frames 60 and 88 are electrically connected to each other by the contact pin 62b and the contact pin receiver 81b connected to the low-frequency outer conductors 44B.

The force required to insert and fit the connecter 21 into the connector receiver 22 corresponds to the friction between the contact pins 62a and 62b and the contact pin receivers 81a and 81b, and it is not desirable to increase this force. However, to enable the user to feel that the connector 21 is fitted, a member such as a C-ring (not shown) may be used so that a clicking action of this member can be felt. Instead, a C-ring or the like may be employed to urge the front-end surface 60D of the outer shielding frame 60 toward the front-end surface 88D of the shielding frame 88 of the connector receiver 22. The insulator plates 66a, 67a, 66b, and 67b are formed by insulating materials.

In the above-described structure of the means for electrically connecting the connector 21 and the connector receiver 22 in accordance with the present invention, the high-frequency signal lines 44 are connected while being shielded by the shielding frames 61 and 82, thereby preventing any noise caused by mixing of a high-frequency signal from entering the low-frequency signal lines 44.

In the thus-constructed first embodiment, two types of shielding are formed: one which is constituted by the outer shielding frame 60, the outer conductors 44B, the cable stop 46, the pipe stop 47, the SID frame 39, and the lens frame 29 to cope with disturbance due to, for example, high-frequency treatment; and one which is constituted by the shielding frame 61 to protect low-frequency signals from high-frequency signals at single-pin connections in the connector means. If no high-frequency treatment is performed, it is not necessary to provide a shielding constituted by the outer shielding frames 60 and 88.

Batch shielding may be effected only for high-frequency lines or low-frequency lines. Both the high-frequency and low frequency lines may be respectively shielded in the batch shielding manner.

In the above embodiment, the shielding frames 60 and 61 as well as the shielding frames 82 and 88 are formed coaxially. However, the arrangement is not limited to this, and these frames may be formed with an eccentric structure. The form of each shielding frame is not necessarily cylindrical and it may have a different shaped cross section. (It may be selected as desired to optimize the layout and reduce the overall size.)

In the above embodiment, signals lines are separated into two groups for high-frequency and low-frequency signals. However, they may be separated into more than two groups while some of the groups are shielded in the batch shielding manner. This arrangement will be exemplified later with respect to a second embodiment.

The above-described first embodiment realizes desired connection based on the single-pin structure, enabling a reduction in the overall size of the connector as well as an increase in the life during repeated connecting and disconnecting operations. Since the signal lines are grouped with respect to high-frequency and low frequency signals, a signal to noise ratio substantially equal to a value in the case of a coaxial-contact connection can be attained.

Figure 4:
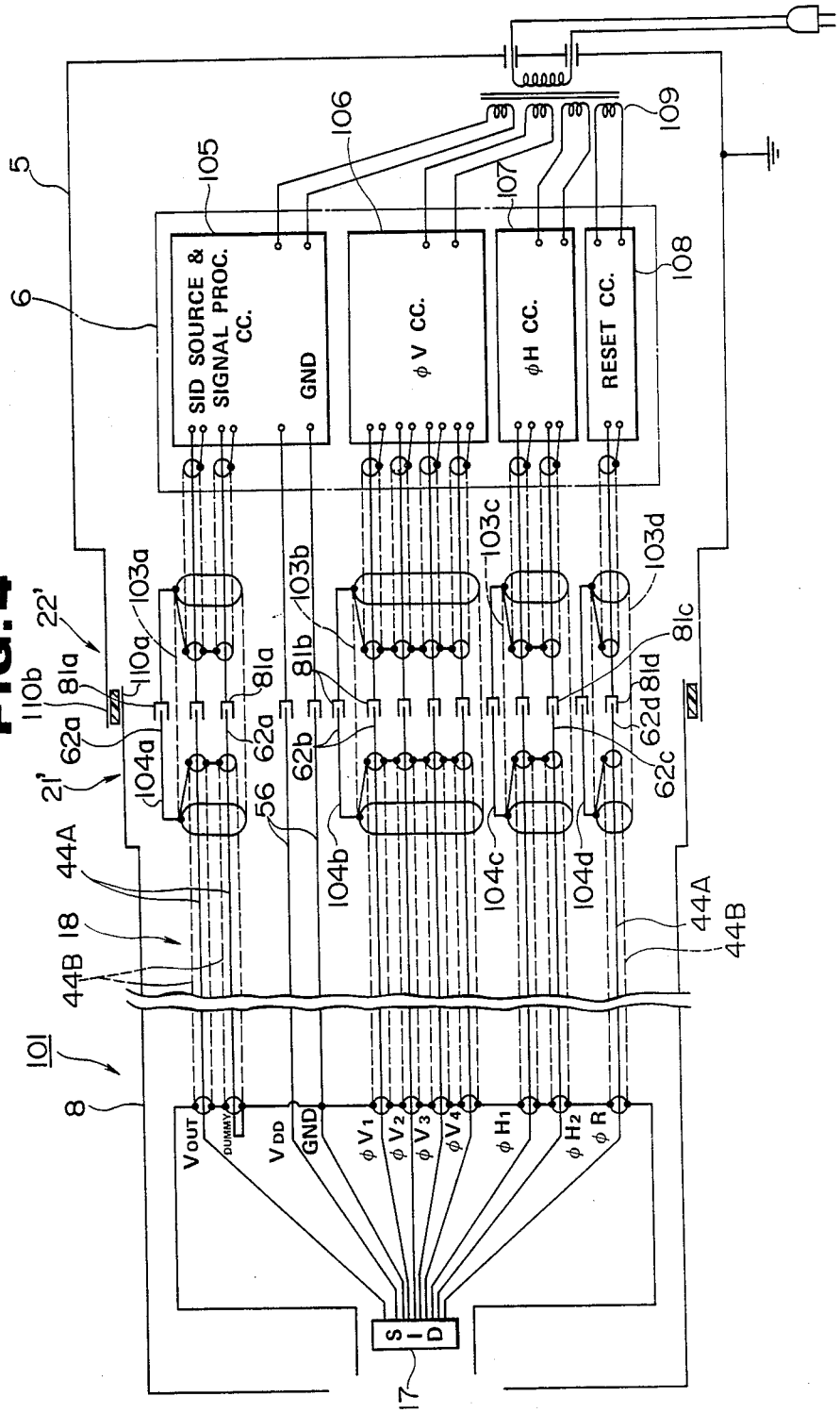
FIG. 4 is a diagram of the structure of essential portions of a second embodiment of the present invention.

FIG. 4 schematically shows the construction of the second embodiment of the present invention in which a plurality of batch shieldings are provided.

Input and output terminals of the SID 17 incorporated in a front end of the insertion portion 8 of an endoscope apparatus 101 are electrically connected to input and output terminals of circuit boards provided in the VP 6 of the signal processing unit 5 via the signal cable 18. The signal cable 18 transmits the following signals: $V_{OUT}$, signals output from the SID (several MHz); DUMMY, noise canceller signals (several MHz); $V_{DD}$, a current (dc) form a power source for driving the SID; $\Phi V_{1\,to\,4}$, vertical synchronizing pulses (several tens KHz); $\Phi H_{1\,and\,2}$, horizontal synchronizing pulses (several MHz); and $\Phi R$, reset pulses (several MHz). Of these signals, $V_{OUT}$, DUMMY, $\Phi V_{1\,to\,4}$, $\Phi H_1$ $_{to\,2}$, and $\Phi R$ are high-frequency signals and each of them acts as a noise source for the lines or components outside its line. Shielding wires are therefore used to form the lines for supplying these signals. Since lines $V_{DD}$ and GND do not act as noise sources for the outside components, they are transmitted by single wires 56. Shielding wires 44 are separated into inner conductors 44A and outer conductors 44B in connection sections of a connector 21' and a connector receiver 22' and are connected by contact pins 62 and contact pin receivers 81. In the signal cable 18, there are certain combinations of high-frequency signals affecting each other by noises or different combinations free from such influences. Therefore, the high-frequency signals transmitted via the cable 18 are separated into four groups: $V_{OUT}$ and DUMMY; $\Phi V_{1\,to\,4}$; $\Phi H_{1\,and\,2}$, and $\Phi R$ (only one line is used for $\Phi R$), and are shielded by batch shielding frames 103a, 103b, 103c, and 103d. The inner conductors are connected by pairs of contact pins 62i (i=a, b, c, d) and contact pin receivers 81i, and the outer conductors 44B are put together into one line which is connected to the shielding frame 103i and is thereafter connected to a contact pin 62i disposed outside the shielding frame 103i and to a contact pin receiver 81i.

The signal lines for $V_{OUT}$ and DUMMY are connected to the SID power source and to a signal processing circuit 105 via the contact pin 62a and the contact pin receiver 81a. The signal lines $V_{DD}$ and GND are respectively connected by the single wires to the SID power source and the signal processing circuit via the contact pin 62 and the contact pin receiver 81.

The signal lines for $\Phi V_{1\ to\ 4}$ are connected to a vertical pulse generating circuit (indicated by $\Phi V$ in FIG. 4) 106 via the contact pin 62b and the contact pin receiver 81b disposed inside the batch shielding frame 103b.

The signal lines for $\Phi H_{1\ and\ 2}$ are connected to a horizontal pulse generating circuit (indicated by $\Phi H$ in FIG. 4) 107 via the contact pin 62c and the contact pin receiver 81c disposed inside the batch shielding frame 103c. The signal line for $\Phi R$ is connected to a resetting circuit 108 via the contact pin 62d and the contact pin receiver 81d disposed inside the batch shielding frame 103d. In the first embodiment, connections of outer conductors 44B of each group are established inside the batch shielding provided for the group. In contrast, in the second embodiment, they are established on the outside.

As shown in FIG. 4, the VP 6 is supplied with power from a commercial power supply through an isolating transformer 109. A line GND of the VP 6 or the SID 17 is thereby isolated and is not connected to a line GND of the signal processing unit 5 or the ground. That is, outer casing members (electroconductive members) 110a and 110b forming outermost peripheral portions of the connector 21' and the connector receiver 22' are isolated by insulating members when the connector and the connector receiver are connected to each other. The outer casing members 110a and 110b are connected to a shielding member which covers the SID 17, and an electroconductive housing member which covers the VP 6 (a case which shields the signal processing unit 5). The shielding case of the signal processing unit 5 is connected to the ground. The lines GND of the SID 17 and the VP 6 are floated from the ground in this manner so that they can be set to the same potential as that of a patient, thereby preventing any electric shock accident.

This embodiment exemplifies the case in which the signal cables 18 are separated into a plurality of groups each of which is shielded in the batch shielding manner, and it is a matter of course that, if the type of the SID 17 changes, the type of the signal cable 18 and the number of lines provided therein become different, and that the present invention can be applied to any case by grouping the lines in accordance with the type of the SID so as to avoid exchange of noises between the lines. In the second embodiment, the metallic head member, the curving portion and the flexible portion are covered with insulating casings as in the case of the first embodiment. Also, the connector portions are connected while being covered with insulating members.

The opening of each outer conductor 44B is positioned inside the opening of the batch shielding frame 103i so that no noise comes through the opening of the shielding frame 103i.

The second embodiment has substantially the same effects as the first embodiment.

Figure 5:
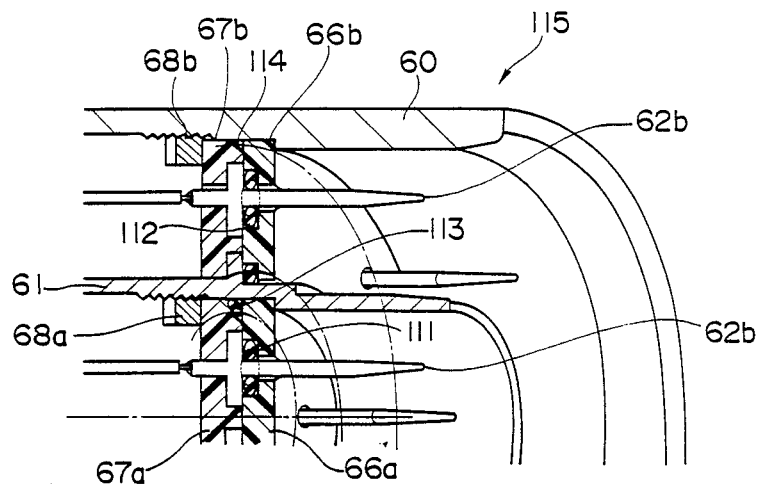
FIG. 5 is a perspective view of part of a signal connector in accordance with a third embodiment of the present invention.

FIG. 5 shows a third embodiment of the present invention. This embodiment includes a waterproofing structure using O-rings (watertight bonding may be adopted instead of O-rings).

The connector 21 shown in FIG. 1 provided as the first embodiment is modified in such a manner that the small holes which are formed in insulator plate 66a and through which the contact pins 62a are made to pass are partially enlarged at the ends thereof on the side of the scope, thereby forming recesses of an increased diameter in which O-rings 111 for enabling watertight connections are accommodated. Similarly, watertight O-rings 112 are accommodated in recesses which are formed in such a manner that the small holes which are formed in insulator plate 66b and through which the contact pins 62b are made to pass are partially enlarged at the ends thereof on the side of the scope. Peripheral edges of the insulator plates 67a and 67b at the surfaces thereof facing the insulator plates 66a and 66b superposed on the insulator plates 67a and 67b are cut like tapers so as to accommodate watertight O-rings 113 and 114, thereby providing a connector 115 of a waterproof structure.

Other portions and constructions are the same as the first embodiment. It is almost impossible to form a connector with a waterproof structure if coaxial-type contacts are used. Conventionally, the user attaches a waterproofing cap to the electrical connector each time he washes the endoscope or plunges it into a chemical liquid. This operation is very troublesome. In addition, if the user inadvertently plunges the endoscope without attaching the cap, water enters the endoscope and it becomes unusable. In such a case, there is even a risk of indirectly damaging the VP. The connector 115 in accordance with the third embodiment has the single-pin structure and it can be constructed with waterproof structures in a simple manner The O-rings 111, 112, 113, and 114 can be disassembled. It is also possible to use a watertight adhesive instead of the O-rings 111, 112, 113, and 114, thereby enabling the size of the structure to be reduced.

Figure 6:
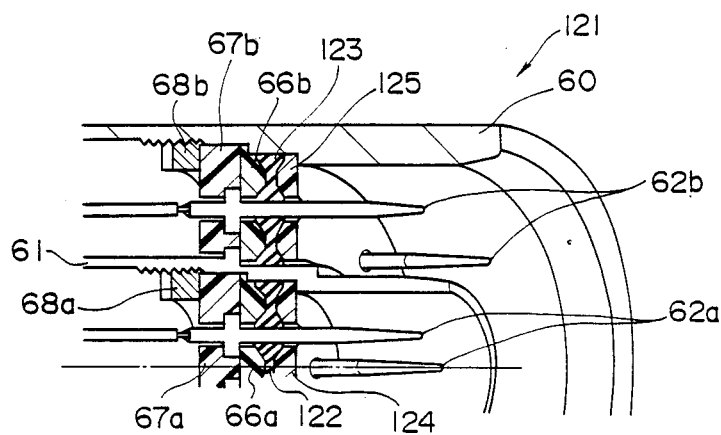
FIG. 6 is a perspective view of part of a signal connector in accordance with a fourth embodiment of the present invention.

FIG. 6 shows essential portions of a connector 121 in accordance with a fourth embodiment of the present invention.

Figure 7:
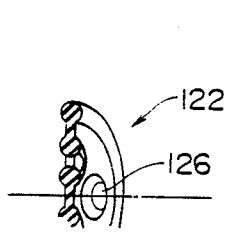
FIG. 7 is a perspective view of one of packings in accordance with the fourth embodiment.
Figure 8:
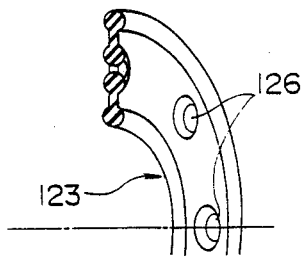
FIG. 8 is a perspective view of the other packing in accordance with the fourth embodiment.

In this embodiment, the connector 21 shown in FIG. 1 has a structure in which a rubber packing 122 in the form of a disk such as the one shown in FIG. 7, and a rubber packing 123 in the form of a disk having a center opening such as the one shown in FIG. 8 are superposed on the surfaces of insulator plates 66a and 66b opposite to the insulator plates 67a and 67b and are pressed on these surfaces by rubber retaining members 124 and 125.

Each of the packings 122 and 123 is provided with small holes 126 which communicate with the small holes formed in the insulator plates 66a or 66bb (through which the contact pins 62a or 62b are made to pass). If each of the small holes 126 is pressed by the insulator plate 66a and the rubber retaining member 124 or by the insulator plate 66b and the rubber retaining member 125, the inner peripheral surfaces of the small hole is brought into close contact with the outer periphery of the contact pin 62a or 62b. The packing is thus designed to enable waterproofing.

Each of the small holes of the insulator plates 66a and 66b through which the contact pins 62a and 62b are made to pass is cut like countersink at its peripheral edge on the side of the packing so that the packing 122 or 123 can be deformed and tightly contact the outer periphery of the contact pin 62a or 62b by an increased contact area when being pressed, thereby improving the waterproofing function. The rubber retaining members 124 and 125 also have small holes which communicate with those of the insulator plates 66a and 66b and each of which has at its peripheral portion a cut similar to a countersink. The corresponding peripheral edge of each of the insulator plates 66a and 66b and the rubber retaining members 124 and 125 is cut like a taper while the thickness of each of the packings 122 and 124 is increased at the outer periphery or at the outer and inner peripheries.

In accordance with the fourth embodiment, each of the packings 122 and 123 is attached or removed by operating the fastening ring 68a or 68, and it can be easily disassembled and replaced, for example, in a case where its properties have become inferior. The structure becomes smaller compared with the above-described arrangement using the O-rings.

Figure 9:
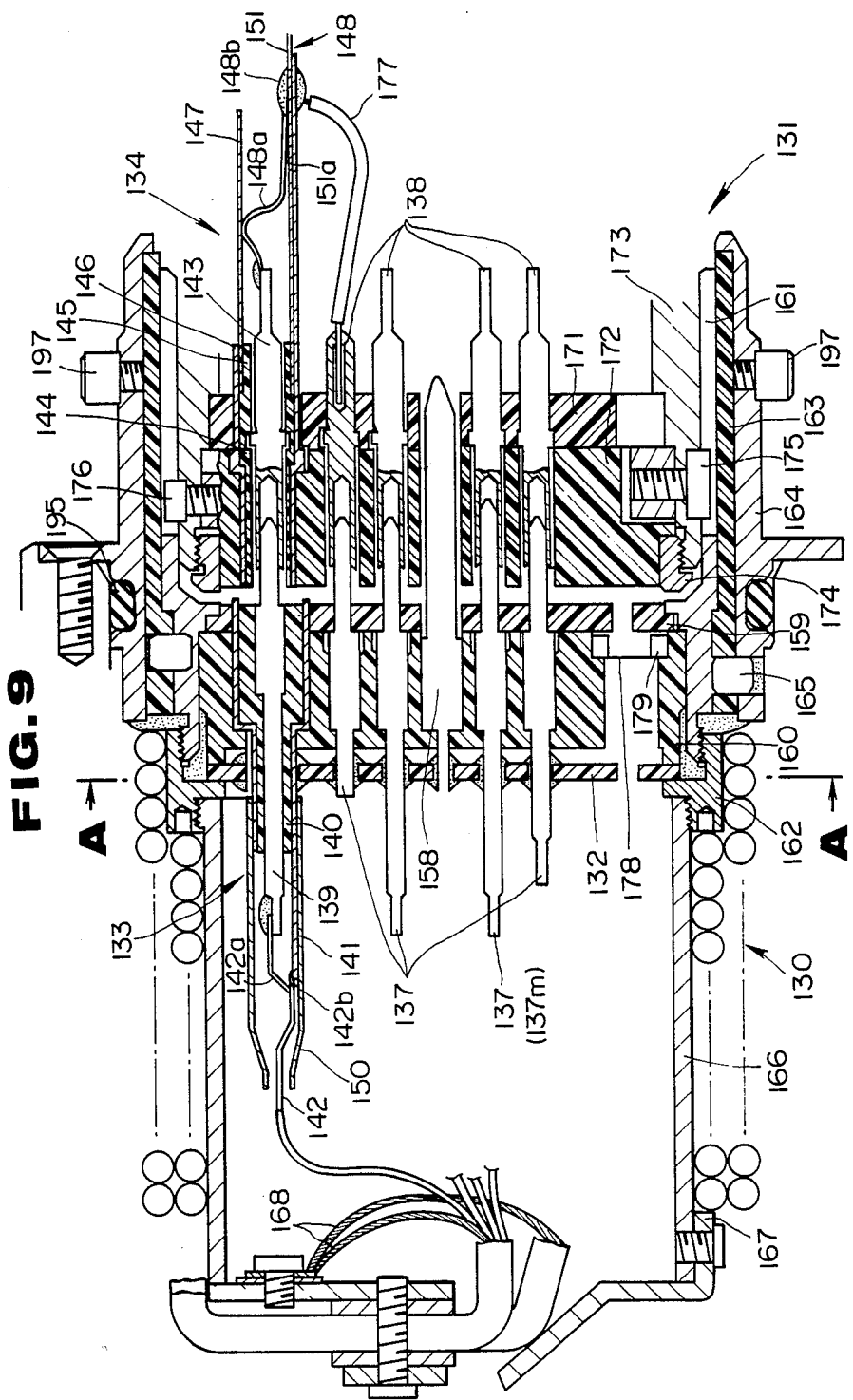
FIG. 9 is a cross-sectional view of the structures of a signal connector and a signal connector receiver in accordance with a fifth embodiment of the present invention.
Figure 10:
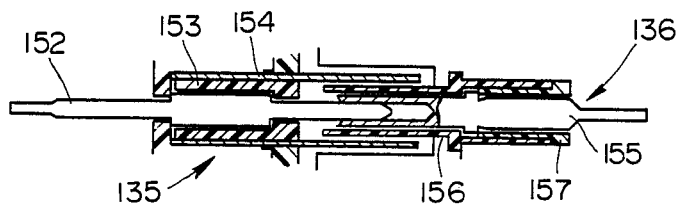
FIG. 10 is a cross-sectional view of part of the signal connector and the signal connector receiver taken on a plane different from that of FIG. 9.
Figure 11:
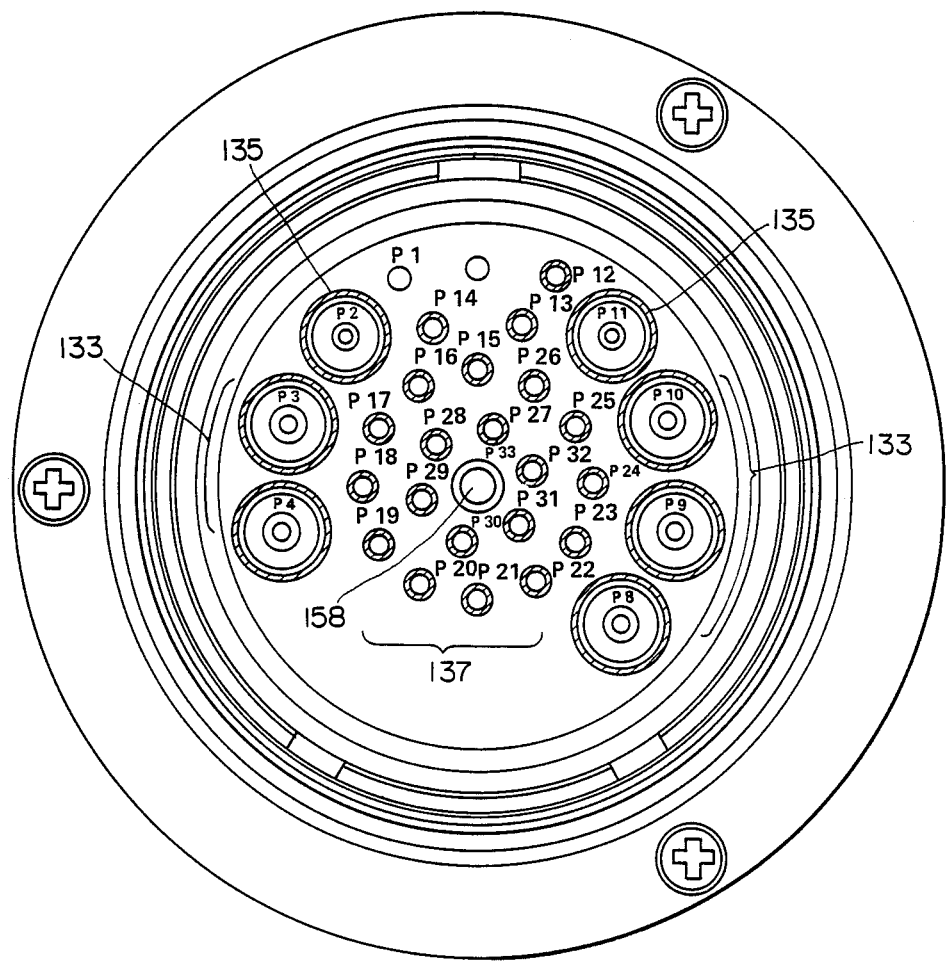
FIG. 11 is a diagram of the disposition of contacts in the signal connector shown in FIG. 9.
Figure 12:
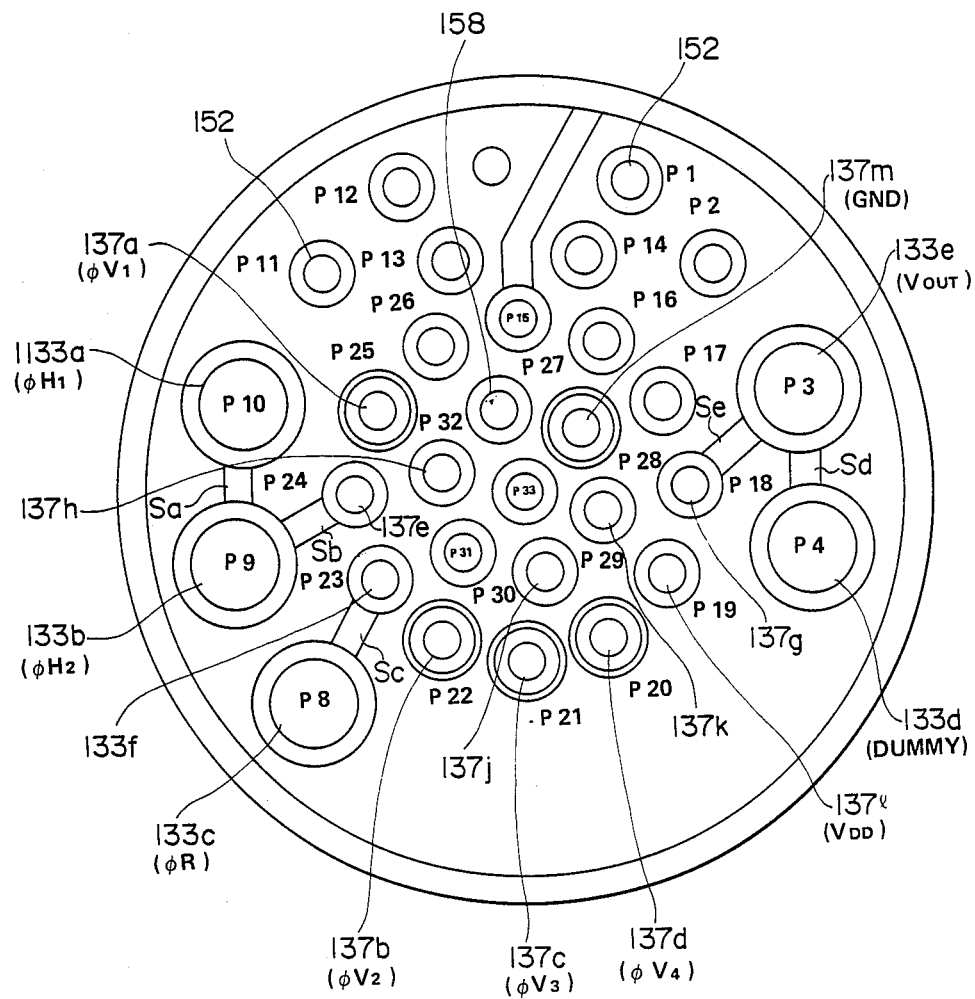
FIG. 12 is a cross-sectional view taken along the line A—A of FIG. 9.
Figure 13:
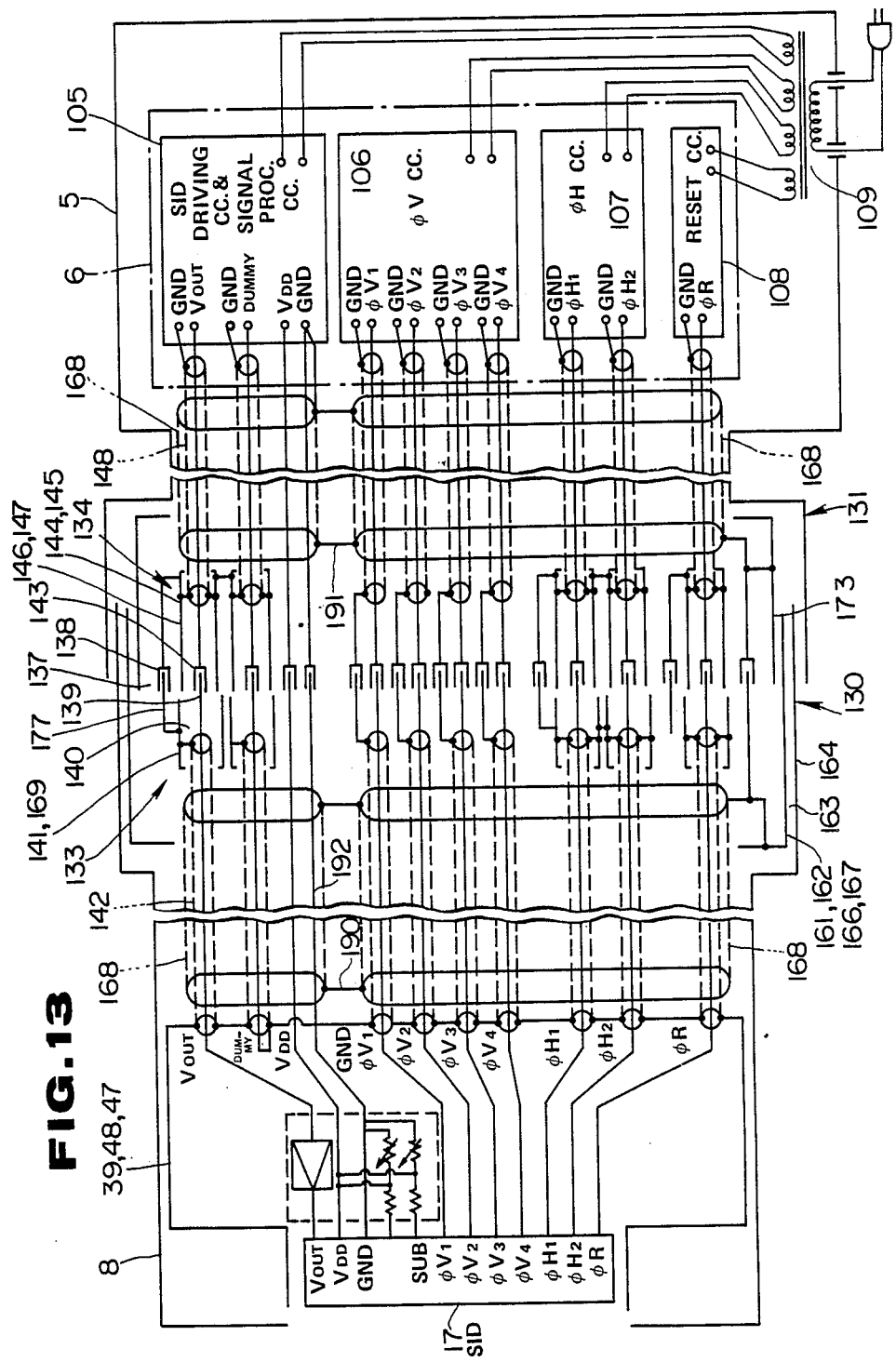
FIG. 13 is a diagram of electrical connections between a solid-state image pickup device and a video processor in accordance with the fifth embodiment.

FIGS. 9 to 14 show a fifth embodiment of the present invention. FIG. 9 shows a connector 130 for transmitting signals and a mating connector receiver 131; FIG. 10 shows portions of them; FIG. 11 shows the disposition of contacts of the signal connector; FIG. 12 shows patterns on a support 132 on a cross-sectional plane taken along the line A—A of FIG. 9; FIG. 13 shows a diagram of electrical connection between the SID 17 and the VP 6; and FIGS. 14(a) and 14(b) show the internal structures of signal cables.

As shown in FIG. 9, contacts in accordance with this embodiment are constituted by shielded contacts 133 and 134, protected contacts 135 and 136, and single-pin contacts 137 and 138. Each of the shielded contacts 133 is constituted by a contact pin 139, an insulating frame 140 which covers the outer periphery of the pin 139, and a shielding frame 141 disposed around the outer periphery of the insulating frame 140. An inner conductor 142a of a coaxial cable 142 is connected to the contact pin 139 while an outer conductor 142b of this cable is connected to the shielding frame 141.

Each of the shielded contacts 134 includes a contact pin receiver 143, insulating members 144 and 145 disposed around the outer peripheries of the contact pin receiver 143 so that they cover front and rear portions thereof, and shielding frames 146 and 147 which cover the insulating members 144 and 145. An inner conductor 148a of a coaxial cable 148 is connected to the contact pin receiver 143 while an outer conductor 148b is connected to the shielding frames 146 and 147.

In the assembly of the shielded contact 134, the insulating member 144, the contact pin receiver 143 and insulating member 145 are successively inserted into the shielding frame 146; the shielding frame 147 is preliminarily put around the coaxial cable 148; the inner conductor 148a is connected to the contact pin receiver 143; the shielding frame 147 is inserted into the shielding frame 146; and the outer conductor 148b is connected by soldering to the shielding frame 146 while the shielding frame 147 is fixed to the shielding frame 146. The shielded contact 134 is thus assembled in a simple manner. An outer covering 151 of the coaxial cable 148 is partially removed only at an intermediate portion of the cable so that part of the covering 151 is left at a portion 151a nearer to the leading end of the cable, thereby preventing the outer conductor 148b from becoming loose. The shielding performance of the coaxial cable is thereby maintained at a portion near the leading end.

A cap 150 for shielding a wiring portion of the cable for connection to the shielded contact 133 is provided around the outer periphery of the shielding frame 141, and this cap and the shielding frame 146 constitute a first shielding means.

Each of the protected contacts 135 is constituted by a contact pin 152, an insulating member 153, and a protective frame 154 and is constructed in such a manner that the contact pin 152 cannot be touched easily. This structure is applied to a portion which may cause an electric shock to the user if he touches this portion.

The other protected contact 136 is constituted by a contact pin receiver 155, and protective frames 156 and 157. The protective frames 156 and 157 are provided for the purpose of limiting the position of the contact pin receiver 155.

A pin 158, which is not of the ordinary type and which is longer than other pins and is connected to a line GND of the circuit, is protrusively disposed in the signal connector 130 generally at the center thereof. If a charged finger of the user is brought closer to the connector, it may contact or become closer to the pin 158 with a certain probability before it contacts the contact pins, thereby protecting the SID 17.

The shielded contacts 133, the protected contacts 135, the single-pin contacts 137 and the pin 158 are assembled on thin and thick insulator plates 159 and 160 and are electrically connected by soldering to the patterns on the support 132. The contacts 133, 135, and 137 are arranged in such a manner that, as shown in FIGS. 11 and 12, the single-pin contacts are disposed in a central area while the shielded contacts are disposed in an outer area.

The pins of the signal connector 130 shown in FIG. 12 are employed to establish connections for supplying signals for driving the SID 17 and signals output therefrom, as shown in FIG. 13.

Shielded contacts 133a and 133b (included in those represented by the shielded contacts 133) are used to connect lines for transmitting horizontal synchronizing pulses $\Phi H_1$ and $\Phi H_2$ at, for example, 8 MHz; a shielded contact 133c is used to connect a line for transmitting reset pulses $\Phi R$ at about 16 MHz; a shielded contact 133d is used to connect a cable for supplying dummy signals at about 16 MHz for eliminating noise mixed in a signal output from the SID 17; a shielded contact 133e is used to connect a line for transmitting an SID output signal at about 16 MHz; and pin contacts 137a, 137b, 137c and 137d are used to connect lines for transmitting vertical synchronizing pulses $\Phi V_1$ to $\Phi V_4$ at about 16 KHz. Among these signals, high-frequency signals cause noises in low-frequency signals and there is no considerable noise exchange between the low-frequency signals. In regard of exchange of noises, therefore, these signals are separated into four groups: one which consists of the vertical synchronizing pulses $\Phi V_1$ and $\Phi V_2$; one which consists of the horizontal synchronizing pulses $\Phi H_1$ and $\Phi H_2$; one which consists of the reset pulses $\Phi R$; and one which consists of the output signal $V_{OUT}$ and the dummy signal.

The output signal $V_{OUT}$ and the dummy Signal are high-frequency signals of about 16 MHz and are analog to each other. The degree of noise exchange between them is small. Therefore, they can be treated in the same group. Also, it is desirable to treat them in the same group in order to equalize the levels of noises mixed in these signals as exactly as possible.

In the first embodiment, these groups of signals are shielded from each other. In this embodiment, however, the contacts for each of the above-described signals (except for vertical synchronizing pulses $\Phi V_1$ and $\Phi V_2$ are shielded contacts as described above, and only portions of the lines to be shielded are grouped, each line being connected by one shielded single-pin contact.

That is, as shown in FIG. 12, shieldings of the horizontal synchronizing pulses $\Phi H_1$ and $\Phi H_2$ are combined into one on pattern elements Sa and Sb and are thereby connected to a single-pin contact 137e. Since the reset pulses $\Phi R$ are supplied via only one line, the shielding of this line is simply connected by a pattern element Sc to a single-pin contact 137f. Shieldings for the output signal $V_{OUT}$ and the dummy signal are combined into one by pattern elements Sd and Se and are connected to a single-pin contact 137g. The group of the vertical synchronizing pulses $\Phi V_1$ to $\Phi V_4$ are not shielded at the signal connector 130 because other signals are shielded. Inner conductors of the lines for these signals are connected to single-pin contacts 137a, 137b, 137c, and 137d while outer conductors are connected to single-pin contacts 137h, 137i, 137j, and 137k. In this case also, the outer conductors may be combined into one for connection to one single-pin contact, but it is difficult to lead and connect four outer conductors to one single-pin contact. Therefore, these outer conductors are separately led and connected to the respective portions. A line for power supply $V_{DD}$ and a line GND are connected to single-pin contacts 137l and 137m, respectively. The contact 137m (shown in FIG. 9) is longer than the other (not shown), and is connected to the single-pin contact 138 faster than the contact 137l when the signal connector 130 is connected to the signal connector receiver 131. When the connector 130 is disconnected from the connector receiver 131, the contact 137m is detached last. This design is intended to avoid a risk of damaging the SID 17 by the application of a signal other than the power supply $V_{DD}$ to the SID 17 prior to the application of power supply $V_{DD}$, which may occur if the connector 130 and the connector receiver 131 are connected to each other while the power source for the VP 6 is supplied with power. Single-pin contacts 137n and 137o are provided for the purpose of detecting the state in which the signal connector 130 and the signal connector receiver 131 are connected to each other. The contacts 137n and 137o are electrically connected to each other via a pattern on the support 132.

The insulator plates 159 and 160 and the support 132 between which these contacts are fixed by a retaining ring 162 inside a guide frame 161 which has a guide groove for insertion of the signal connector receiver 131 into the signal connector 130. An insulating frame 163 is provided around the outer periphery of the guide frame 161, and an electrical connector adaptor 164 is disposed around the insulating frame 163 and is positioned and fixed by angle pins 165.

The guide frame 161 and the retaining ring 162 constitute a second shielding means for shielding wiring portions of the cables inside the connector. The retaining ring 162 is connected to an end of a shielding frame 166 which is included in the second shielding means, and the other end of the shielding frame 166 is connected by a screw to a member 167 which is also included in the second shielding means. The member 167 is electrically connected to overall shieldings 168 of the cables. Wiring portions of the cables led and connected to the shielded contacts 133 are shielded by the caps 150 which, together with the shielding frames 146, constitutes the first shielding means.

Figure 14A:
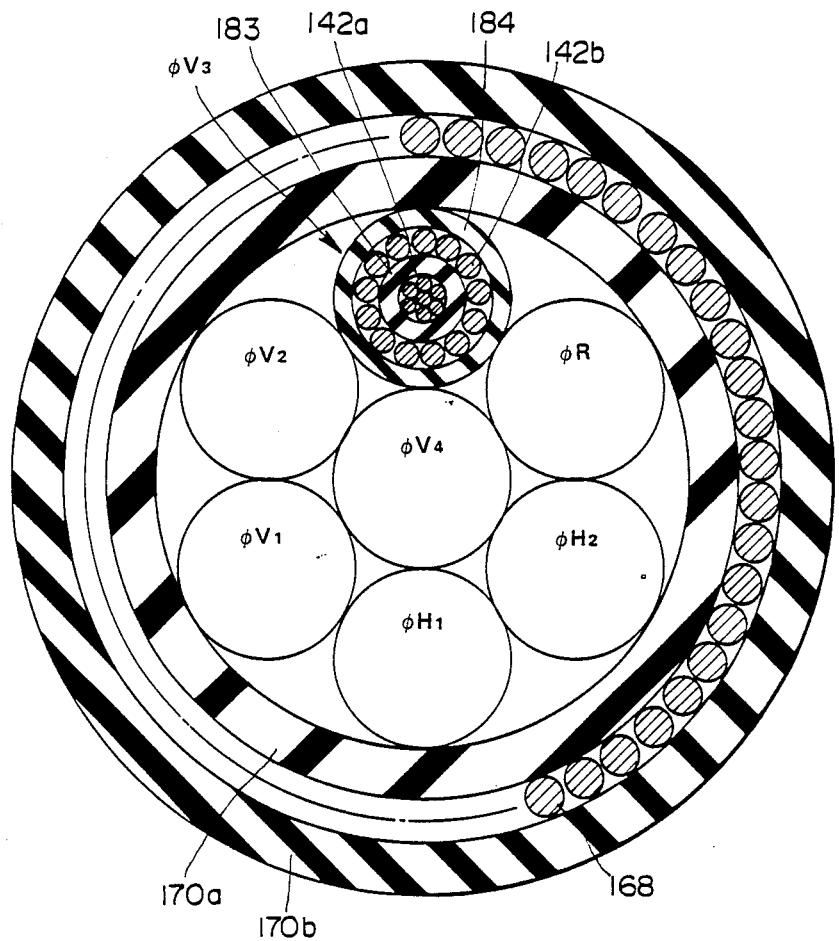
FIGS. 14(a) and 14(b) are cross-sectional views of cables illustrating the structures thereof.
Figure 14B:
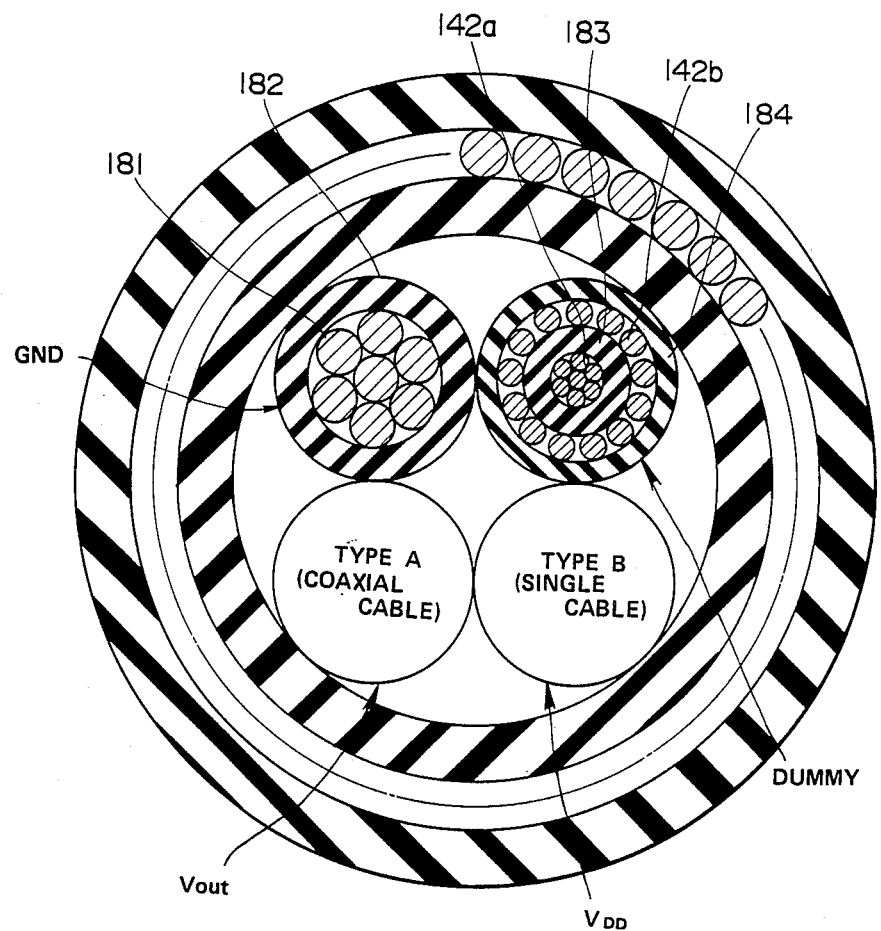

In this embodiment, the overall shielding 168 is formed in such a manner that, as shown in FIGS. 14(a) and 14(b), a group of seven and another group of four cables are formed from the SID signal cables; each group is bundled and covered with a insulating tape 170a; the overall shielding 168 is formed around the outer periphery of this covering; and the outer periphery of the shielding 168 is covered with an outer covering sheath 170b having insulating properties.

The overall shieldings 168 are electrically connected to the second shielding means so that a double shielding structure is formed over the cables extending from the circuit boards of the VP 6, the signal connector receiver 131, the signal connector 130 and the cables connected to the SID 1, thereby providing doubly increased shielding effects.

On the other hand, the signal connector receiver 131 is constructed in such a manner that shielded contacts 134, the protected contacts 136 and the single-pin contact 138 are pinched between thin and thick insulator plates 171 and 172, are thereafter fitted to a connector mouth member 173, and are fixed by a retaining ring 174. At this point, the insulator plates 171 and 172 are positioned by angle pins 175 and 176 which also serve as guides for fitting the signal connector receiver 131 to the signal connector 130. Since all of the pins of the signal connector 130 are fixed, a structure in which the contacts of the signal connector receiver 131 are fixed to the insulator plates 171 and 172 cannot be adopted because of the need for absorbing play of the contacts, and it is not possible to connect the cables by soldering. For this reason, each of connections between the shielding frame 146 and 147 and the single-pin contacts 138 (corresponding to the patterns on the support 132) is established by a jumper wire 177.

When the signal connector 130 and the signal connector receiver 131 are fitted to each other, the caps 150 and the shielding frames 141, 146, and 147 constitute the first shielding means while the shielding frame 166, the member 167, the guide frame 161, the retaining ring 162 and the connector mouth member 173 constitute the second shielding means. The first shielding means is connected to the outer conductors of the respective cables while the second shielding means are connected to the overall shielding means 168. The second shielding means is connected to the electrical connector adaptor 164 with the insulating frame 163 interposed therebetween, and is therefore insulated from the outer covering metal. This structure can prevent influences of disturbance introduced by the outer covering metal (e.g., high-frequency noise). As shown in FIG. 9, the first shielding means has a gap for preventing the shielding frames 141 and 146 from contacting each other, and the electrical connection therebetween is established by the single-pin contacts separately provided. This design is intended to avoid an increase in the force required to connect and disconnect the connector and the connector receiver which may be caused by the contact between the shielding frames. Also, this structure prevents a signal transmitted through the shielded contacts from being disturbed by variations in the characteristic impedance of the shielded contacts caused by contacting and non-contacting states of the shielding frames. That is, the characteristic impedance is constantly maintained.

FIG. 14(a) shows a structure in which each of seven signal lines is formed as a coaxial line, and FIG. 14(b) shows a structure in which signal lines GND and $V_{DD}$ are constituted by single-wire cables (type B) each formed of a group of conductors 181 covered with a covering 182 while a Signal line $V_{OUT}$ and a dummy Signal line are constituted by coaxial cables (type A) similar to those shown in FIG. 14(A). In each coaxial cable, inner conductors 142a are covered with internal covering 183, outer conductors 142b are disposed around the outer periphery of the covering 183, and an outer covering 184 are formed around the outer conductors 142b. These groups of cables are shielded by overall shieldings 168 to for double shielding structures.

The effects of the shielding slightly change depending upon whether or not conductors 190 and 191 are used to connect the shieldings, as shown in FIG. 13. If the conductor 190 is used, the shielding performance against high-frequency emission noises caused by the internal coaxial cables is improved, but a closed circuit is formed between the overall shieldings 168 and GND 192 with a certain inductance, which receives high frequency noises. The shielding performance against external high-frequency noises is thereby slightly reduced. On the other hand, if the conductor 190 is not used, no closed circuit is formed and the shielding becomes highly effective against external high-frequency noises, but (internal) emission noises coming through openings in the vicinity of the SID 17 increase. The same can be said with respect to the conductor 191. These conductors may therefore be provided in accordance with the desired use.

However, in the former case, the overall shielding 168 is not electrically connected to the SID frame 39, the pipe 48 and the pipe stop 47, and it is preferable to uniformly cover them with loosened shielding wires like wrapping as closely as possible.

A sheet 178 provided in the signal connector 130 permits only air supplied via a pressure mouth piece provided in a waterproofing cap (not shown) to pass though itself while being impermeable to water when this cap is put on the electrical connector adapter 164. The sheet 178 is fixed by a ring 179 in a waterproofing manner. Therefore, there is no risk of water entering the connector when the user inadvertently plunges it into water without fitting the cap. Correspondingly, component parts of each of the contacts 133 and 135 are fixed to each other in a waterproofing manner to form the waterproof contact. The contacts 133, 135, and 137, and the pin 158 are fixed to the insulator plate 160 is a watertight manner. Also, the insulator plate 160, the guide frame 161, the insulator frame 163, and the electrical connector adaptor 164 are interconnected in a watertight manner. A watertight O-ring 195 is fitted in an outer peripheral portion of the electrical connector adaptor 164. Guide pins 195 are used to fit a waterproofing cap (not shown) to a cam ring (not shown) which is used when the signal connector receiver 131 is inserted.

There is provided only one combination of the signal connector 130 and the signal connector receiver 131 in the arrangement shown in FIG. 13. However, it may be replaced with a plurality of connector sets. It is natural that the number of signal lines and the signal frequencies are changed depending upon the type of the SID 1. The signal lines may be grouped in accordance with these factors.

In accordance with this embodiment, the shielding frame of the shielded contact does not function as a contact, and a single-pin contact superior in durability is used to connect the shieldings, thereby improving the durability of the connector.

In the case of the signal connector 130, each shielding contact can be easily provided with a waterproof structure, enabling the overall waterproofed connector.

Figure 15:
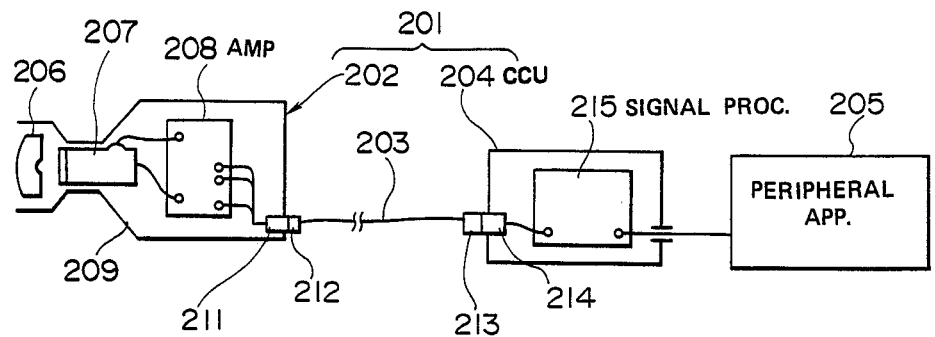
FIG. 15 is a diagram of a sixth embodiment of the present invention.

FIG. 15 shows an image pickup apparatus 201 which represents a sixth embodiment of the present invention.

The image pickup apparatus 201 is constituted by an image pickup section 202 and a CCU 204 connected via a signal cable 203. The CCU 204 may be connected to a peripheral unit 205 such as a display in order to display an obtained image or may record the image by a recording unit such as a video tape recorder.

An image pickup tube 207 is disposed at the focal plane of an objective 206 in the image pickup section 202. A signal obtained by photoelectric transfer in the image pickup tube 207 is amplified by an amplifier circuit 208 and is introduced to a signal connector receiver 211 attached to a housing 209 of the image pickup section 202. A connector 212 attached to an end of a signal cable 203 is connected to the connector receiver 211, and a connector 213 attached to the other end of the cable 203 is connected to a connector receiver 214 of the CCU 214, thereby enabling the signal amplified by the amplifier circuit 208 to be transmitted to the CCU 204. The transmitted signal is processed in a signal processing circuit (video processor) 215 provided in the CCU 204 so that it is converted into an NTSC composite image signal or RGB signal.

The connectors and connector receivers in accordance with the above-described embodiments can be applied to the connectors 212 and 213 and the connector receivers 211 and 214.

Figure 16:
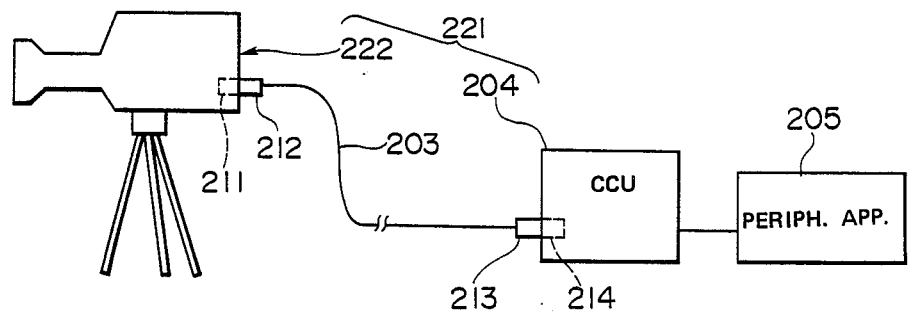
FIG. 16 is a diagram of a seventh embodiment of the present invention.

FIG. 16 shows an image pickup apparatus 221 which represents a seventh embodiment of the present invention.

The image pickup apparatus 221 is constituted by applying a TV camera 222 to the image pickup section of the apparatus in accordance with the sixth embodiment.

The TV camera 222 is provided with the connector receiver 211 to which the connector 212 of the signal cable 203 can be connected.

In this embodiment also, the above-described types of connectors can be used as the connectors 212 and 213. The same can also be said with respect to the connector receivers 211 and 214.

Figure 17:
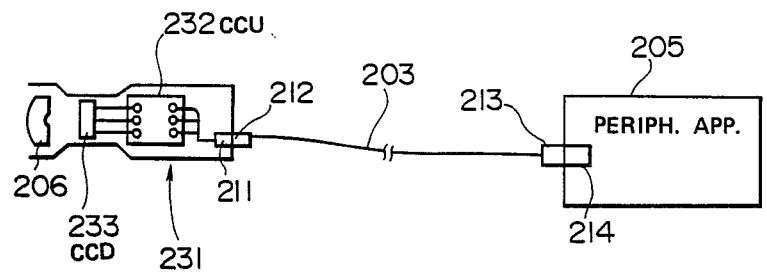
FIG. 17 is a diagram of a eighth embodiment of the present invention.

FIG. 17 shows an image pickup apparatus 231 which represents an eighth embodiment of the present invention.

The image pickup apparatus 231 is constituted by a camera which incorporates a CCU 232. In this embodiment, a CCD 233 is disposed at the focal plane of the objective 206 and is connected to the CCU 232 via signal lines.

In this embodiment, the image pickup apparatus 231 and the peripheral device 205 are provided with the signal connector receivers 211 and 214, respectively. The connectors 212 and 213 are connected to the connector receivers 211 and 214, thereby transmitting signals.

The above-described types of connectors and connector receivers can be used as the connectors 212 and 213 and the connector receivers 211 and 214. The connector 212 and 213 may be of the same structure or of different types of structure. The same can be said with respect to the signal connector receivers 211 and 214.

In accordance with the present invention, as described above, a shielding cable is separated inside the signal connector into inner and outer conductors for single-pin connection, and signal cables are connected while being separated into groups in each of which signals in different cables do not influence each other by noises, each group being shielded in batch shielding manner, enabling a reduction in the size of the structure of the electrical connector as well as improvements in durability and S/N.

What is claimed is:

1. A video endoscope system comprising:
   an image pick up means including photoelectric transfer function;
   a video processor supplying a driving signal to said image pick up means and receiving an image signal from the image pick up means;
   an electrical connection device for connecting said image pick up means and said video processor;
   a plurality of contacting means for respectively transmitting said driving signal, a video signal and the like;
   a first shielding means for electrically shielding the plurality of contacting means transmitting a vertical synchronizing pulse of the driving signal from among the plurality of contacting means; and
   a second shielding means, electrically separated from said first shielding means, for shielding said contacting means transmitting said video signals.

2. A video endoscope system according to claim 1 further comprising a third shielding means, electrically separated from said first and second shielding means, for shielding the contacting means transmitting a horizontal synchronizing pulse of said driving signal.

3. A video endoscope system according to claim 1 wherein said plurality of contacting means consisting of respective pins and pin receivers and said first and second shielding means respectively comprising a contacting means for connecting with a grounding conductor consisting of a pair of pins and pin receivers.

* * * * *

UNITED STATES PATENT AND TRADEMARK OFFICE
CERTIFICATE OF CORRECTION

PATENT NO. : 4,974,075
DATED : November 27, 1990
INVENTOR(S) : Shigeru NAKAJIMA

It is certified that error appears in the above-identified patent and that said Letters Patent is hereby corrected as shown below:

On the cover page, Item [75], delete "Fuchu" and substitute therefor --Tokyo--.

Signed and Sealed this

Twenty-eighth Day of April, 1992

Attest:

HARRY F. MANBECK, JR.

*Attesting Officer*     *Commissioner of Patents and Trademarks*